United States Patent
Matsuda et al.

(10) Patent No.: US 6,593,153 B2
(45) Date of Patent: Jul. 15, 2003

(54) METHOD OF AND APPARATUS FOR MEASURING LATTICE-CONSTANT, AND COMPUTER PROGRAM

(75) Inventors: Takeyoshi Matsuda, Tokyo (JP); Satoru Seo, Tokyo (JP); Kengo Mitose, Tokyo (JP)

(73) Assignee: The Furukawa Electric Co., Ltd., Tokyo (JP)

( * ) Notice: Subject to any disclaimer, the term of this patent is extended or adjusted under 35 U.S.C. 154(b) by 0 days.

(21) Appl. No.: 10/027,491

(22) Filed: Dec. 20, 2001

(65) Prior Publication Data

US 2002/0166965 A1 Nov. 14, 2002

(30) Foreign Application Priority Data

Mar. 16, 2001 (JP) .................................... 2001-077136

(51) Int. Cl.[7] .............................................. H01L 21/66
(52) U.S. Cl. .......................................... 438/14; 438/47
(58) Field of Search ................... 438/14, 47; 257/18, 257/190; 356/72

(56) References Cited

U.S. PATENT DOCUMENTS

| | | | | |
|---|---|---|---|---|
| 4,086,001 A | * | 4/1978 | Chen et al. ................. 385/130 |
| 4,855,013 A | * | 8/1989 | Ohta et al. .................. 117/85 |
| 5,132,981 A | * | 7/1992 | Uomi et al. .................. 257/18 |
| 5,679,965 A | * | 10/1997 | Schetzina .................... 257/103 |
| 5,936,716 A | * | 8/1999 | Pinsukanjana et al. ...... 117/202 |
| 5,997,638 A | * | 12/1999 | Copel et al. .................. 117/89 |
| 6,038,017 A | * | 3/2000 | Pinsukanjana et al. ...... 356/72 |
| 6,046,464 A | * | 4/2000 | Schetzina .................... 257/190 |
| 6,130,147 A | * | 10/2000 | Major et al. .................. 438/47 |
| 6,252,261 B1 | * | 6/2001 | Usui et al. .................... 257/190 |
| 6,426,515 B2 | * | 7/2002 | Ishikawa et al. ............. 257/14 |
| 2002/0050288 A1 | * | 5/2002 | Suzuki ........................ 136/255 |

FOREIGN PATENT DOCUMENTS

| JP | 07-106260 A | 4/1995 | ......... H01L/21/205 |
|---|---|---|---|
| JP | 2000-046762 A | 2/2000 | ......... G01N/23/20 |

OTHER PUBLICATIONS

X.F. Duan, "Thin film relaxation in cross–sectional transmission election microscopy specimens of $Ge_x Si_{1-x}$/Si strained–layer superlattices," Appl. Phys. Lett. 66 (17), Apr. 24, 1995, pp. 2247–2249.

* cited by examiner

*Primary Examiner*—John F. Niebling
*Assistant Examiner*—Olivia T Luk
(74) *Attorney, Agent, or Firm*—Sheppard Mullin Richter & Hampton LLP

(57) ABSTRACT

A condenser angle of 0.5 mrad or below is set with respect to a specimen. Electron-beam diameter of 20 to 100 nm φ is set onto the surface of the specimen. A flux of highly parallel electron beams is irradiated onto the specimen having a strained layer quantum well structure. An image of electrons diffracted from the specimen is recorded onto an imaging plate. The recorded image is analyzed. Lattice constants and strains of layers of the strained layer quantum well structure are measured based on a result of this analysis.

20 Claims, 15 Drawing Sheets

METHOD OF AND APPARATUS FOR MEASURING LATTICE-CONSTANT, AND COMPUTER PROGRAM

FIELD OF THE INVENTION

The present invention relates to a technology capable of measuring efficiently and in high precision a lattice constant of a specimen having a multi-layer film structure in a nano-meter order like a strained layer quantum well structure that is employed in a semiconductor laser element.

BACKGROUND OF THE INVENTION

Along the development of semiconductor technologies in recent years, it has become possible to easily form a multi-layer film structure in a nano-meter order. As a result, it has become possible to provide a semiconductor laser element having a strained layer quantum well structure, for example, which makes it possible to obtain efficient laser light-emission characteristics.

In the semiconductor laser element having such a strained layer quantum well structure, it is necessary to evaluate actual strain of a lattice. It is possible to evaluate such a strain by measuring a lattice constant. As a method for measuring a lattice constant, generally measurements are performed using a diffraction image based on the Bragg diffraction.

As a method for measuring a lattice constant, there is the X-ray diffraction (XRD) method. In the X-ray diffraction method, X-rays are irradiated onto a specimen to be evaluated, and then a lattice constant of the specimen is obtained by computer simulation based on an X-ray diffraction image diffracted from the rotated specimen. According to this X-ray diffraction method, it is necessary that the specimen at least has an area of 1 mm×1 mm where measurement can be per-formed.

On the other hand, as methods for measuring a lattice constant using the transmission electron microscope (TEM), there are the selected-area electron diffraction (SAD) method (see FIG. 15A), the nano-beam electron diffraction (NBD) method (see FIG. 15B), and the condenser-beam electron diffraction (CBD) method (see FIG. 15C). These methods are used for obtaining an electron diffraction image according to a transmission electron beam that has passed through a specimen by irradiating an electron beam onto the specimen.

In the selected-area electron diffraction method, as shown in FIG. 15A, all electron beams that pass through a condenser lens 133 are irradiated onto a specimen 112 by maintaining these electron beams substantially in parallel, and an electron diffraction image is obtained from a fine area that is limited by a fine hole of a selected-area aperture 137 disposed between an objective lens 135 and an intermediate lens 138. In the selected-area electron diffraction method, the minimum measuring range is 200 nm$\phi$, and the spread of diffraction spots is $10^{-5}$ to $10^{-6}$ rad. Further, the measurement precision of a lattice constant to be analyzed is about 3 digits.

In the nano-beam electron diffraction method, as shown in FIG. 15B, a small electron beam of a condenser angle that has been converged to a nano-meter order through the condenser lens 133 and the condenser aperture 134 is irradiated onto the specimen 112, thereby to obtain an electron diffraction image. In the nano-beam electron diffraction method, the minimum measuring range is 2 nm$\phi$, and the spread of diffraction spots is $10^{-3}$ to $10^{-4}$ rad. Further, the measurement precision of a lattice constant to be analyzed is about 2 digits.

In the condenser-beam electron diffraction method, as shown in FIG. 15C, a large electron beam of a condenser angle that has been converged to a nano-meter order through the condenser lens 133 and the condenser aperture 134 is irradiated onto the specimen 112, thereby to obtain an electron diffraction image. A computer simulation is carried out based on this electron diffraction image, and a lattice constant of the specimen is obtained based on a result of this simulation. The computer simulation is carried out because the electron diffraction image obtained according to the condenser-beam electron diffraction method becomes a complex diffraction image. In the condenser-beam electron diffraction method, the minimum measuring range is 2 nm$\phi$, and the spread of diffraction spots is $10^{-2}$ to $10^{-3}$ rad. Further, as an electron diffraction image having a large volume of information is obtained, the measurement precision of a lattice constant is about 4 digits.

However, in case of measuring a lattice constant of a strained layer quantum well active layer having a multi-layer film structure in a nano-meter order, the measuring range becomes 5 to 500 nm. Therefore, there is a drawback that it is not possible to obtain a sufficient electron diffraction image when the X-ray diffraction method having a minimum measurement range of 1 mm×1 mm or the selected-area electron diffraction method having a minimum measurement range of 200 nm$\phi$ is used, as their measurement range of a specimen is too small. As a result, these methods have had a problem that it is not possible to measure a lattice constant of a strained layer quantum well active layer.

Further, in case of measuring a lattice constant of a strained layer quantum well active layer by using the nano-beam electron diffraction method that has a minimum measurement range of 2 nm$\phi$, the precision of measuring the lattice constant is not sufficiently high. Therefore, there has been a problem that it is not possible to obtain a necessary enough level of precision.

Further, in case of measuring a lattice constant of a strained layer quantum well active layer by using the condenser-beam electron diffraction method, as the minimum measurement range of 2 nm$\phi$, and the measurement precision of a lattice constant is about 4 digits, it is possible to measure in high precision a lattice constant of each layer that constitutes the strained layer quantum well active layer. However, there has been a problem that it is difficult to measure in high precision the lattice constant of the strained layer quantum well active layer in which the lattice constant of each layer has periodicity.

In other words, even if it is possible to measure in high precision the lattice constant of each layer of the strained layer quantum well active layer by using the condenser-beam electron diffraction method, it is difficult to measure the lattice constant of each layer based on the same measuring condition. Particularly, in the strained layer quantum well active layer, each layer has a spatial strain distribution. Therefore, there has been a problem that it is not possible to accurately measure an average strain of the lattice constants based on a simple averaging of lattice constants through a discrete measurement of each layer.

SUMMARY OF THE INVENTION

It is an object of the present invention to provide a method of and an apparatus for measuring a lattice constant capable of measuring promptly and in high precision the average value of the lattice constants of layers that form a multi-layer film structure in a nano-meter order like a strained layer quantum well active layer. It is another object of this invention to provide a computer program that contains instructions which when executed on a computer realizes the method according to the present invention on the computer.

The method of measuring a lattice constant according to one aspect of the present invention comprises following processes. That is, a flux of highly parallel electron beams are irradiated onto a specimen having a multi-layer film structure in a nano-meter order. Then, an electron diffraction image diffracted from the specimen is recorded onto a photosensitive member. Finally, the recorded electron diffraction image is analyzed, and a lattice constant of a multi-layer film structure of the specimen is measured based on a result of the analysis.

The apparatus for measuring a lattice constant according to another aspect of the present invention irradiates a flux of electron beams onto a specimen, records an electron diffraction image based on a diffraction of the electron beams passed through the specimen, and analyzes the electron diffraction image and measures a lattice constant of the specimen. Moreover, there is provided a condenser aperture at an electron beam source side of the specimen having a strained layer quantum well structure. With this arrangement, a fine flux of electron beams having a condenser angle of 0.5 mrad or below and having an electron-beam diameter of 20 nm to 100 nm are irradiated onto the specimen.

Other objects and features of this invention will become apparent from the following description with reference to the accompanying drawings.

DESCRIPTION OF THE PREFERRED EMBODIMENTS

Embodiments of a method of an apparatus for measuring a lattice constant, and the computer program according to the present invention will be explained below with reference to the accompanying drawings.

Figure 1:
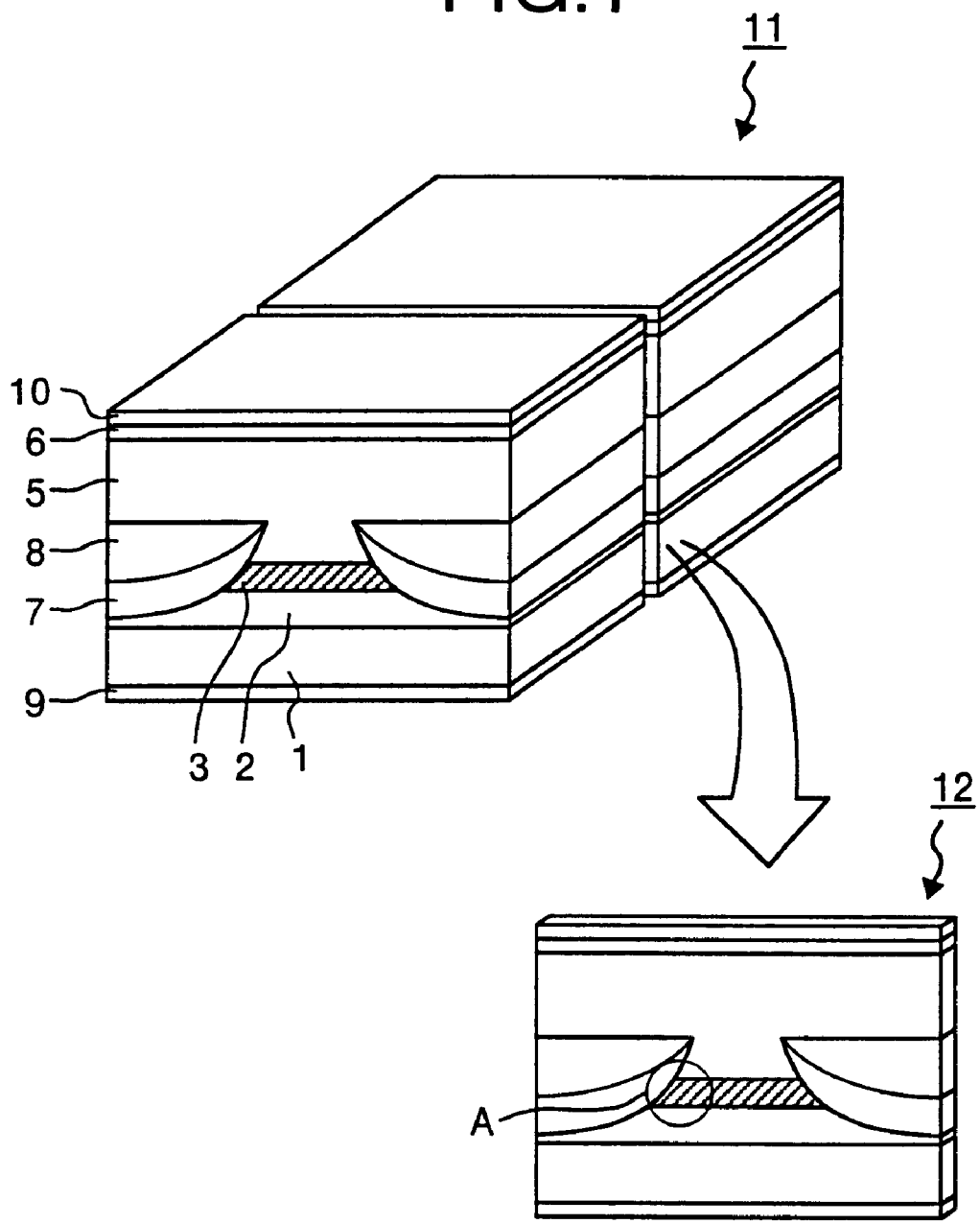
FIG. 1 is a view showing a structure of a semiconductor laser element from which a specimen according to a first embodiment of the present invention is extracted, and a structure of this specimen.

FIG. 1 is a view showing a semiconductor laser element as a specimen to be measured by a method of measuring a lattice constant according to a first embodiment of the invention. As shown in FIG. 1, the semiconductor laser element 11 has the n-InP buffer layer 2 working both as a buffer layer and a lower clad layer of n-Inp, the active layer 3 formed by an SCH-MQW (separate confinement heterostructure multi-quantum well) layer having a strain, the p-InP clad layer 5, and the InGaAsP cap layer 6. These layers are laminated in sequence on the n-InP substrate 1.

A lower portion of the p-InP clad layer 5, the active layer 3, and an upper portion of the buffer layer 2 are processed in a mesa stripe shape. Both sides of the mesa stripe are buried with a p-InP blocking layer 7 and an n-InP blocking layer 8 formed as current blocking layers, thereby to realize a buried semiconductor laser element. A p-side electrode 10 is formed on the upper surface of the InGaAs cap layer 6, and an n-side electrode 9 is formed on the back surface of the n-InP substrate 1.

A specimen 12 is obtained by slicing the semiconductor laser element 11 in a direction perpendicular to a longitudinal direction (a resonance direction) of the semiconductor laser element 11. The thickness of the specimen 12 is preferably about 100 nm. An irradiation area A of the specimen 12 is an area onto which a flux of electron beams to be described later are irradiated.

Figure 2:
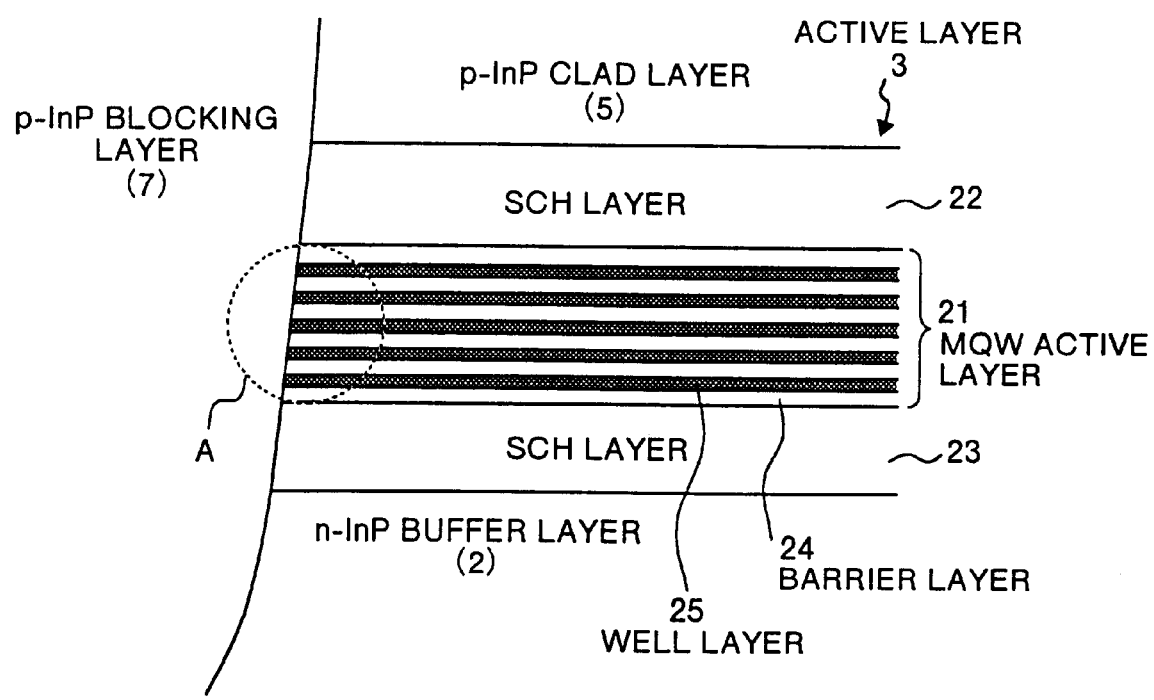
FIG. 2 is an enlarged view of the specimen shown in FIG. 1.

FIG. 2 is an enlarged view of portions near the irradiation area A of the specimen 12. As shown in FIG. 2, the active layer 3 has the MQW active layer 21 of a multi-layer film structure that has been formed by repeatedly laminating a barrier layer 24 and the well layer 25 with strains. On the upper and lower layers of the MQW active layer 21, there are laminated SCH layers 22 and 23 as light-sealing layers respectively. The barrier layer 24 and the well layer 25 are formed with GaInAsP, and their stoichiometric ratios are different. A lattice constant of the barrier layer 24 is smaller than a lattice constant of InP (the n-InP blocking layer 7). A lattice constant of the well layer 25 is larger than a lattice constant of InP. The irradiation area A covers the MQW active layer 21 and the p-InP blocking layer 7, and this is the area substantially around the boundary between the MQW active layer 21 and the p-InP blocking layer 7. It is not always necessary to bring this boundary to the center, and it is possible to narrow the area of the InP blocking layer 7 according to the needs.

Figure 3:
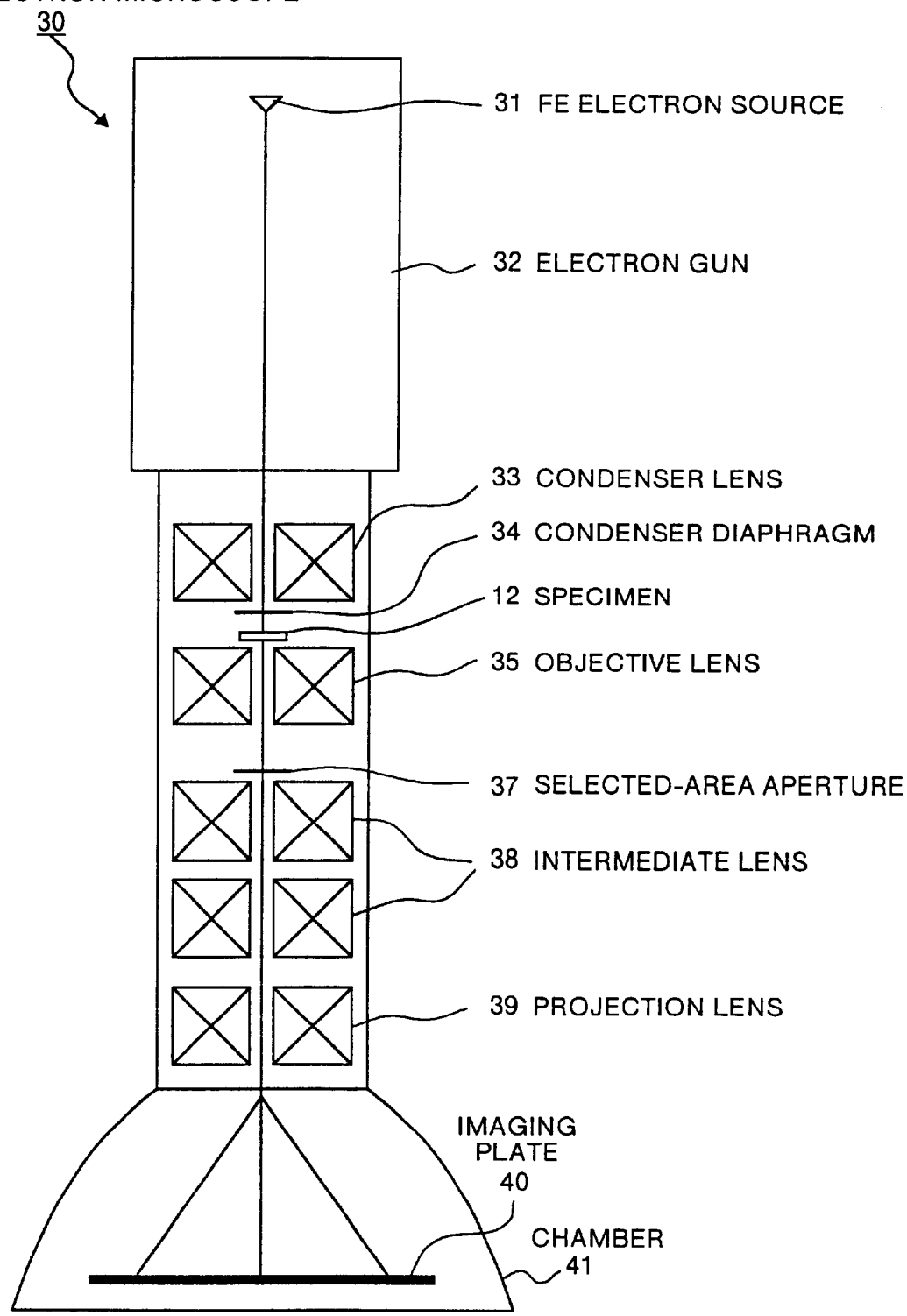
FIG. 3 is a cross-sectional view showing an outline structure of a field-emission transmission electron microscope according to the first embodiment of the invention.

FIG. 3 is a cross-sectional view showing an outline structure of a field-emission transmission electron microscope for obtaining an electron diffraction image of the specimen 12. This field-emission transmission electron microscope 30 handles electron beams emitted from the electron gun 32 like visible optical beams with an electromagnetic lens like the condenser lens 33, and forms an electron diffraction image on the imaging plate 40 after the electron beams have been transmitted through the specimen 12. The imaging plate 40 is placed in the chamber 41 In this case, as the electron beams have a shorter wavelength than the visible optical beams, this field-emission transmission electron microscope can execute measurement in higher scale factor than an optical microscope. The electromagnetic lens generates a magnetic field that distributes in a convex shape when a current flows through a coil, and works as a convex lens for the electron beams. The FE electron source 31 within the electron gun 32 applies an electric field to a W (tungsten) chip to generate electron, as this is a field-emission type. The diameter of this electron beam is smaller than that of an electron beam generated from a general-electron source by flowing a current to a tungsten filament.

Figure 15A:
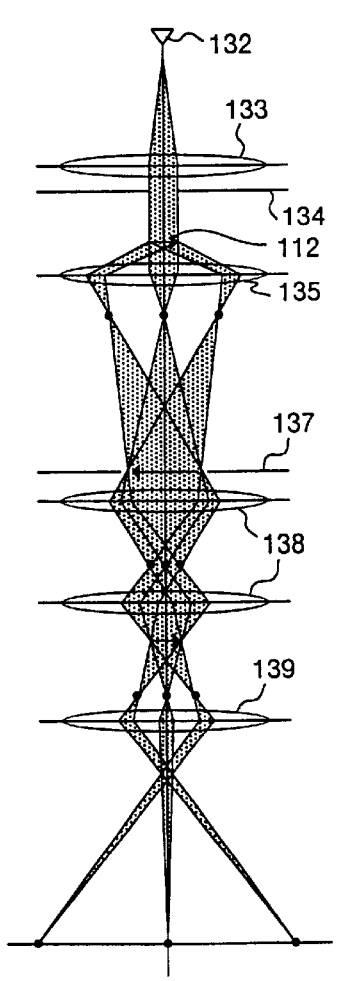
FIGS. 15A to 15C are schematic views for explaining a selected-area electron diffraction method, a nano-beam electron diffraction method, and a condenser-beam electron diffraction method that are conventional methods respectively.
Figure 15B:
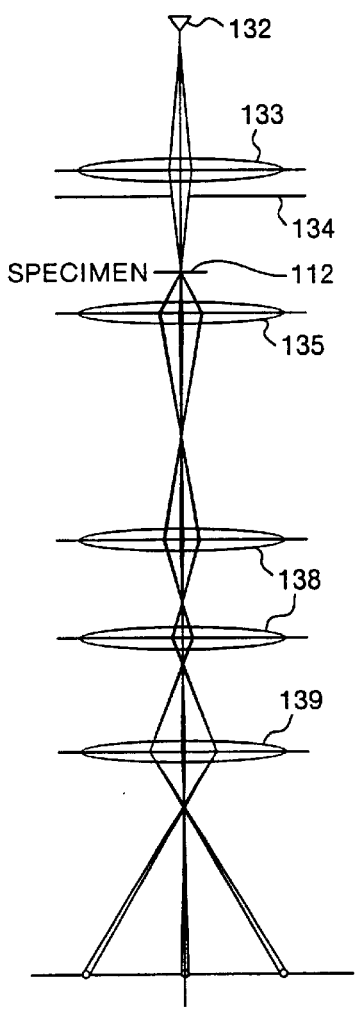
Figure 15C:
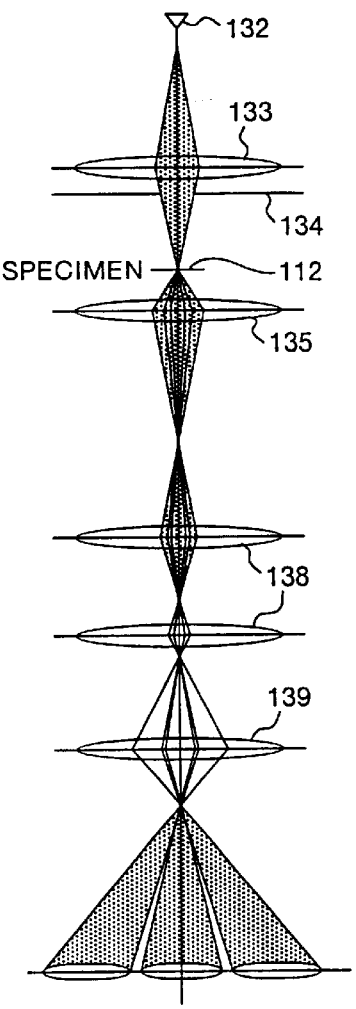

The electron beams output from the FE electron source 31 are output as an electron diffraction image onto the imaging plate 40, through the condenser lens 33, objective lens 35, intermediate lens 38, and the projecting lens 39, substantially in a similar manner to that of the nano-beam electron diffraction method shown in FIG. 15B. The condenser aperture 34 is provided between the condenser lens 33 and the objective lens 35. The condenser aperture 34 diaphragms the flux of electron beams converged by the condenser lens 33. The specimen 12 is mounted between the condenser aperture 34 and the objective lens 35. Then, electron beams diaphragmed by the condenser aperture 34 are irradiated on this specimen 12. The electron beams having passed through the specimen 12 are formed as an electron diffraction image on the imaging plate 40 through the objective lens 35, intermediate lens 38, and the projection lens 39.

Figure 4:
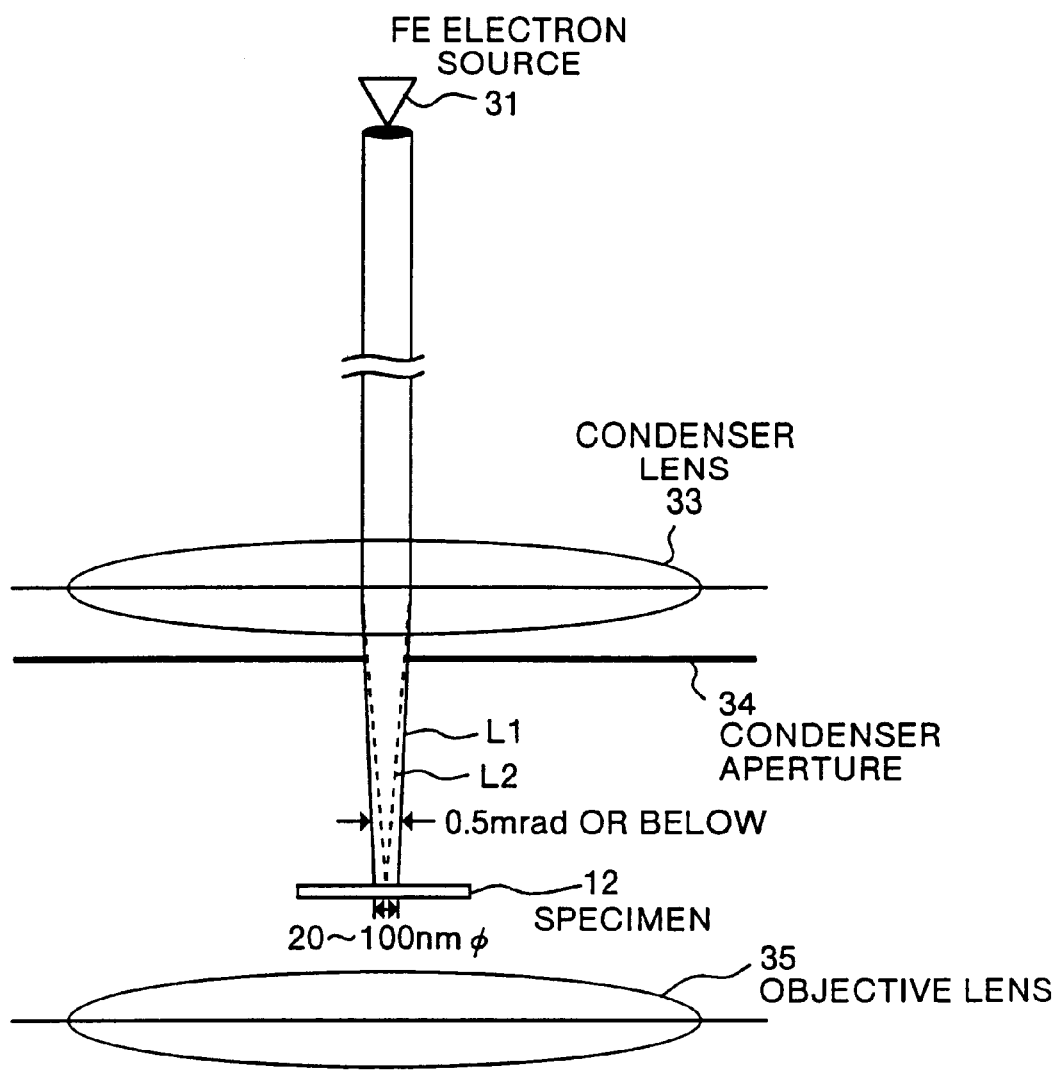
FIG. 4 is a cross-sectional view showing a structure of portions near a condenser lens of the field-emission transmission electron microscope and the specimen shown in FIG. 3.

FIG. 4 is a cross-sectional view showing a structure of a portion near the condenser lens 33 of the field-emission transmission electron microscope 30 and the specimen 12 shown in FIG. 3 As shown in FIG. 4, a flux of electron beams emitted from the FE electron source 31 are converged by the condenser lens 33. The converged beams are then diaphragmed into a fine flux of electron beams by the condenser aperture 34, in a similar manner to that of the nano-beam electron diffraction method. As this diaphragmed flux of electron beams are output from the FE electron source 31, the beams are highly in parallel. Further, the electron beams have a condenser angle of 0.5 mrad or below from the aperture hole of the condenser aperture 34 to the specimen. Further, the electron beams maintain the parallel. Further, the diameter of each electron beam on the surface of the specimen 12 is 20 to 100 nmφ. This electron-beam diameter matches the irradiation area A.

An electron beam flux L1 is the electron beam flux according to the first embodiment. An electron beam flux L2 is the electron beam flux according to the nano-beam electron diffraction method shown in FIG. 15B. The conventional electron beam flux L2 has been adjusted such that the focus of the condenser lens 33 matches on the specimen 12. On the other hand, according to the electron beam flux L1 in the first embodiment, it is possible to obtain the constant irradiation area A. Further, the focus of the condenser lens 33 is set between the specimen 12 and the objective lens 35. As a result, the flux L1 of electron beams that are highly in parallel are irradiated onto the constant irradiation area A, and it is possible to simultaneously obtain the electron diffraction image of each layer in the multi-layer film structure like a strained layer quantum well structure. In other words, an electron diffraction image similar to that of an electron diffraction image of a specimen having one constant lattice constant obtained by the nano-beam electron diffraction method can be obtained simultaneously as a plurality of electron diffraction images for the layers of the multi-layer film structure. In this case, the electron diffraction images of the respective layers are superimposed as independent electron diffraction images.

The specimen 12 is based on the Bragg condition that only the diffracted wave of a (001) plane (where 1 is a natural number) as a substrate orientation that is the same as the growth direction of each layer that constitutes the MQW active layer 21, is strongly exited.

In the first embodiment, it is assumed that a period d of the strained layer quantum well structure is 5 to 50 nm, a wavelength λ of an electron beam is 0.0025 nm (200 kV), and a Bragg angle is θ. Then, from the following equation of Bragg, $$2d \sin \theta = \lambda$$

the Bragg angle θ of a multiple quantum well structure is expressed as follows:

$$\theta = \sin^{-1}(\lambda/2d)$$

The Bragg angle θ becomes 0.025 to 0.25 mrad. As a result, the condenser angle is set to 0.25 mrad or below.

Figure 5:
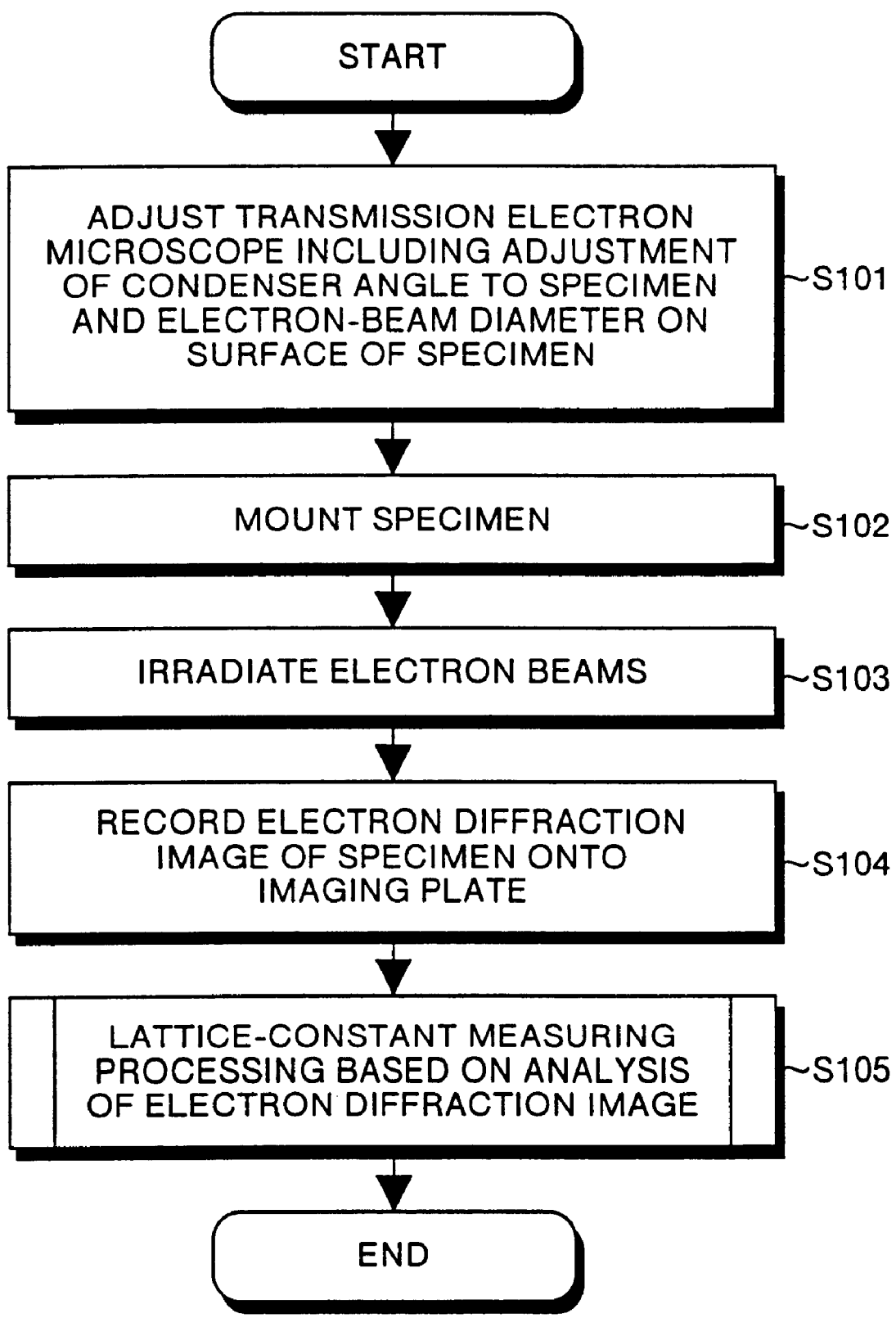
FIG. 5 is a flowchart showing a processing procedure of a method of measuring a lattice constant according to the first embodiment of the invention.

The method of measuring a lattice constant according to the first embodiment of the present invention will be explained with reference to a flowchart shown in FIG. 5. First, a sliced specimen 12 is prepared. Then, the field-emission transmission electron microscope 30 is adjusted including the adjustment of a condenser angle to the specimen 12 and an electron-beam diameter on the surface of the specimen (step S101).

The specimen 12 is mounted on the field-emission transmission electron microscope 30 (step S102). Electron beams are irradiated onto the specimen 12 from the FE electron source 31 (step S103). An electron diffraction image of this specimen 12 is recorded on the imaging plate 40 (step S104).

Finally, a lattice-constant measuring processing is carried out based on an analysis of the electron diffraction image recorded on the imaging plate 40 (step S105). The lattice-constant measuring processing based on the analysis of the electron diffraction image is executed by the apparatus for measuring a lattice constant shown in FIG. 6.

The imaging plate 40 is used as the recording member of an electron diffraction image because the imaging plate 40 has a large dynamic range to an electron beam intensity. In general, a slow-scan CCD camera and an electron microscope film are used for recording an electron diffraction image. The dynamic range of the slow-scan CCD camera is about three digits, and the dynamic range of the electron microscope film is about two digits. Considering the resolution of electron diffraction images when the electron diffraction images of the layers of a multi-layer film structure have been superimposed with each other, it is necessary to take at least five digits for the dynamic range, as it is necessary to read high-order electron diffraction images. The imaging plate 40 is one of recording members that has the dynamic range of five digits or above. Therefore, in the first embodiment, the imaging plate 40 is used as a recording member of electron diffraction images.

The imaging plate 40 is an imaging sensor having a shape of a film on which an accelerated phosphorescent phosphor that can be used repeatedly is coated. A recorded electron diffraction image is scan-irradiated with laser beams so that the electron diffraction image is phosphorated again. This phosphorous status is read as image data.

Figure 6:
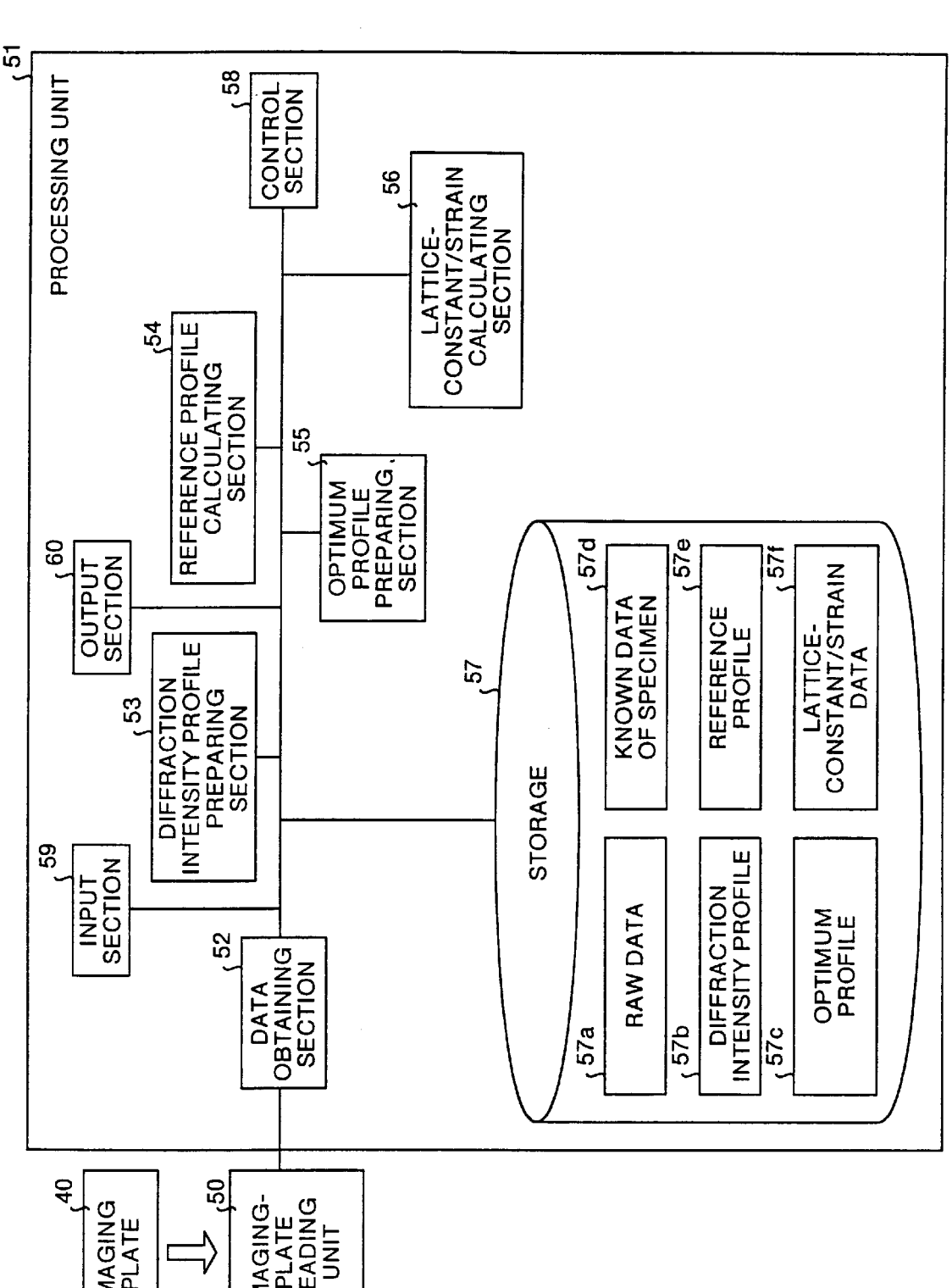
FIG. 6 is a block diagram showing a structure of an apparatus for measuring a lattice constant according to the first embodiment of the invention.
Figure 7:
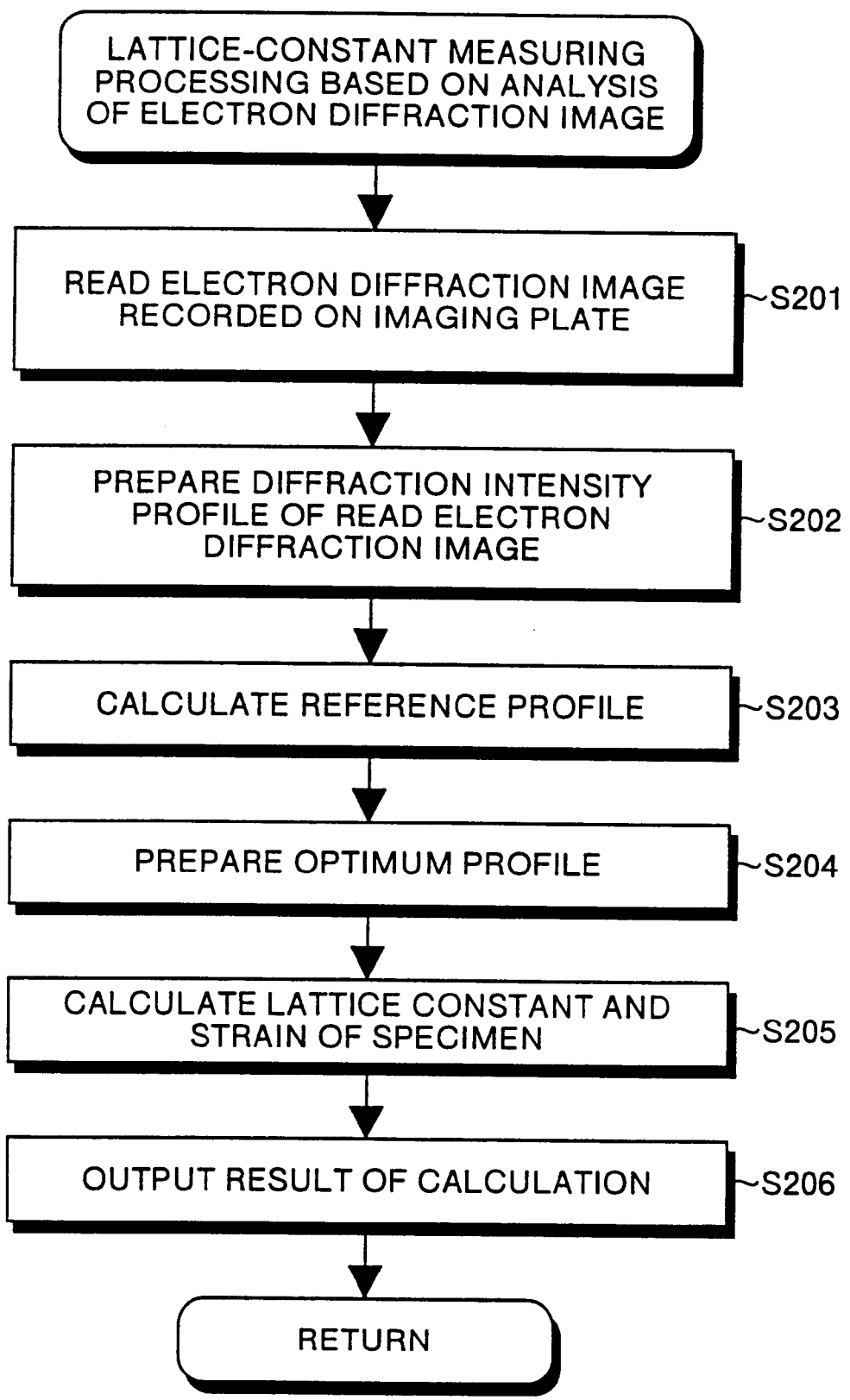
FIG. 7 is a detailed flowchart showing a procedure of measuring a lattice constant based on the analysis of an electron diffraction image shown in FIG. 5.

FIG. 6 is a block diagram showing a structure of the apparatus for measuring a lattice constant according to the first embodiment of the invention. This apparatus for measuring a lattice constant has an imaging plate reading unit 50, and a processing unit 51. The imaging plate reading unit 50 reads an electron diffraction image recorded on the imaging plate 40 as digital information. The digital information is obtained by scan-irradiating the laser beams as described above.

The processing unit 51 has a data obtaining section 52. The data obtaining section 52 obtains imaged data of the electron diffraction image read by the imaging plate reading unit 50, and stores this as raw data 57a of a storage 57. A diffraction intensity profile preparing section 53 prepares a diffraction intensity profile that shows a profile of diffraction intensity at a diffraction position, based on the raw data 57a. The diffraction intensity profile preparing section 53 stores this profile as a diffraction intensity profile 57b in the storage 57. This diffraction intensity profile 57b may display the coordinates of the diffraction position by converting the data into reciprocal lattice coordinates.

The reference profile calculating section 54 calculates in advance a diffraction intensity profile of an electron diffraction image of the reciprocal lattice coordinates by simulation, based on known data 57d of the specimen previously obtained about the specimen 12. The reference profile calculating section 54 stores a result of this calculation as a reference profile 57e in the storage 57. The known data 57d of the specimen such as a number of lattices in each layer can be obtained from a TEM image that has been obtained by using this field-emission transmission electron microscope 30.

The optimum profile preparing unit 55 changes a parameter of the reference profile 57e to generate a profile as an optimum profile 57c that fits most as the diffraction intensity profile 57b. The optimum profile preparing unit 55 stores this optimum profile 57c into the storage 57.

The lattice-constant/strain calculating section 56 determines an average lattice constant of each layer, and calculates a strain of the lattice constant, based on the optimum profile 57c. The average lattice constant and the strain of each layer are stored as the lattice constant/strain data 57f, in the storage 57.

The input section 59 is an input unit for inputting input instructions. This input section 59 is realized by a keyboard and a pointing device. The output section 60 is for displaying or printing out information instructed by the input section 59. This output section 60 is realized by a CRT display and/or a printer. The control section 58 controls the total processing of the sections within the processing unit 51.

The lattice-constant measuring processing (step S105) based on the analysis of an electron diffraction image will be explained with reference to FIG. 7 to FIG. 12. First, the imaging plate reading unit 50 reads the electron diffraction image recorded on the imaging plate 40 (step S201). The data obtaining section 52 stores the read electron diffraction image as the raw data 57a into the storage 57.

Figure 8:
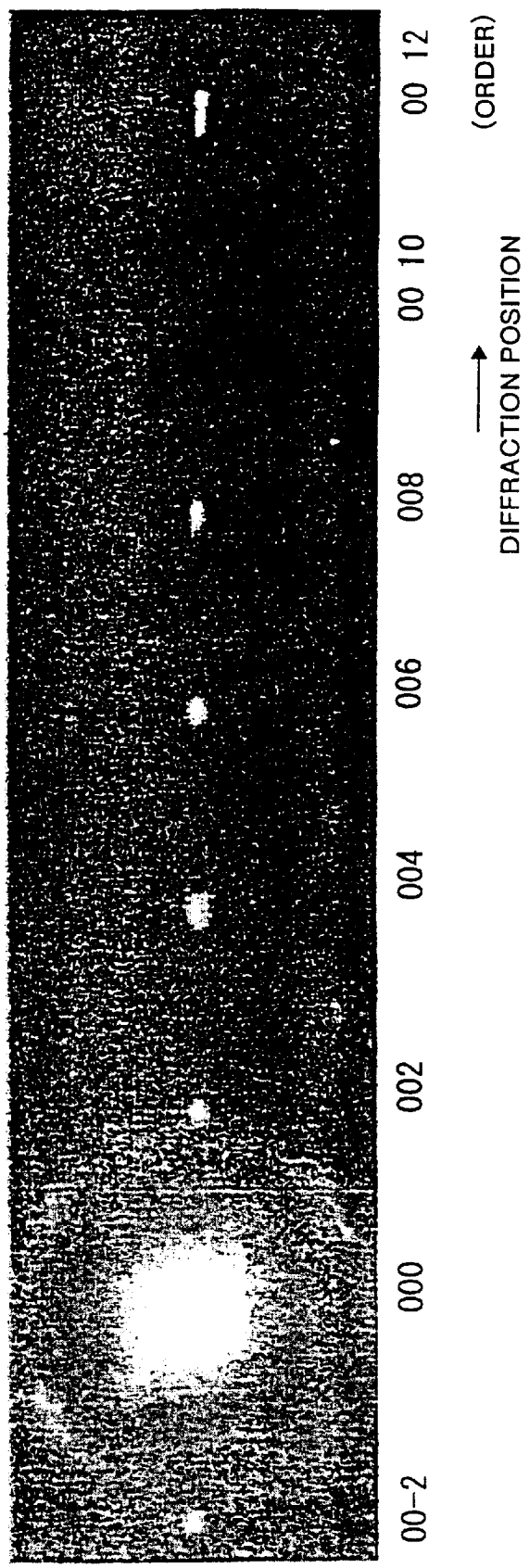
FIG. 8 is a view showing one example of an electron diffraction image.
Figure 9:
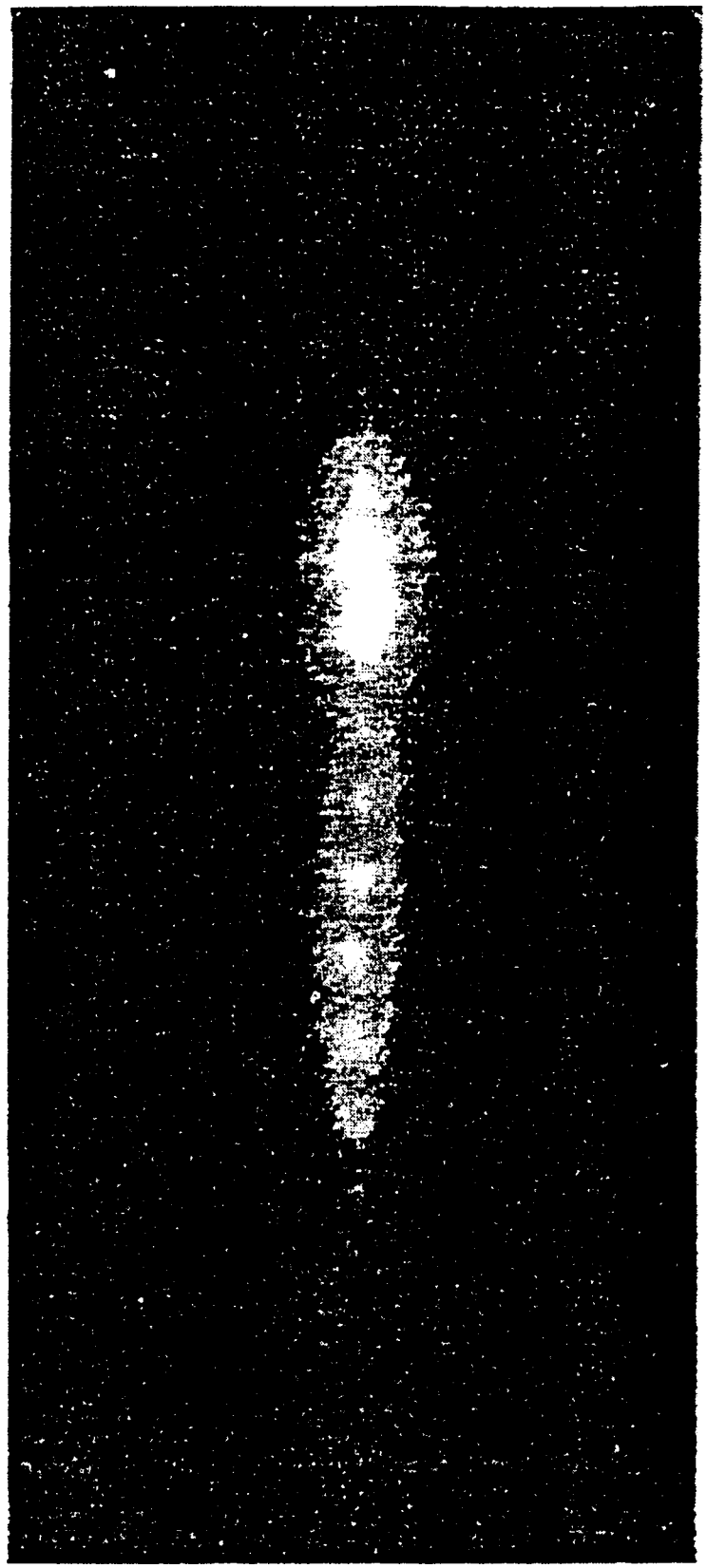
FIG. 9 is an enlarged view of a twelfth electron diffraction image of the electron diffraction image shown in FIG. 8.
Figure 10:
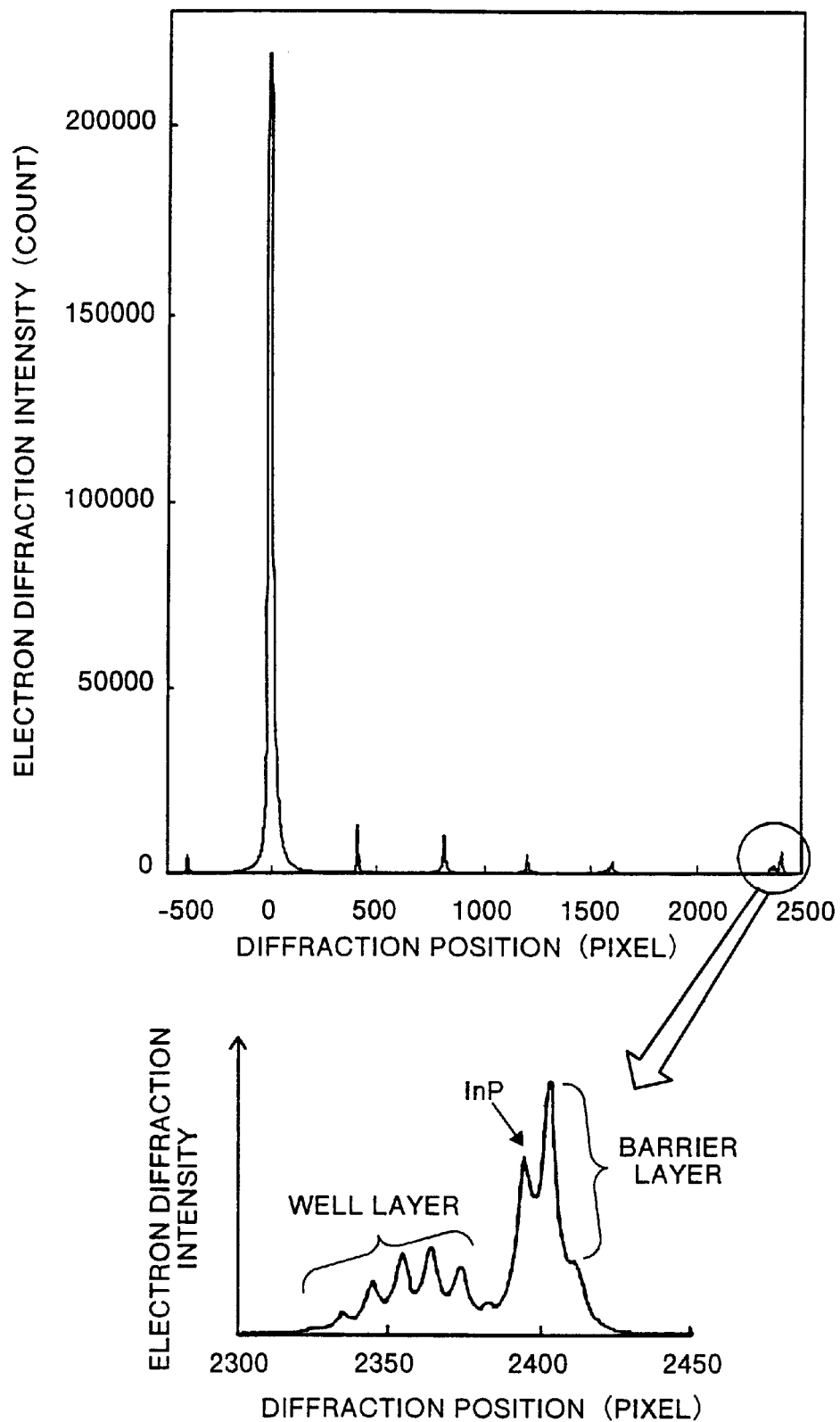
FIG. 10 is a diagram showing diffraction intensity profiles shown in FIG. 8 and FIG. 9.

Thereafter, the diffraction intensity profile preparing section 53 prepares the diffraction intensity profile 57b based on the raw data 57a (step S202). For example, FIG. 8 is an electron diffraction image of the specimen 12 stored on the imaging plate 40. FIG. 9 is an enlarged view of a twelfth electron diffraction image. The diffraction intensity profile preparing section 53 prepares a profile of the electron diffraction intensity at the diffraction position as shown in FIG. 10, based on the electron diffraction images shown in FIG. 8 and FIG. 9.

The diffraction intensity of a zero-order electron diffraction image is 200 thousand in terms of the number of counts, and the diffraction intensity of the twelfth electron diffraction image is about 1000 at the most. Therefore, in order to draw the profile of the twelfth electron diffraction image, the imaging plate 40 that has the dynamic range of five digits is used as described above.

In the twelfth electron diffraction image, the barrier layer 24 having a smaller lattice constant than the lattice constant of InP appears based on Inp, at a diffraction position larger than the diffraction position of InP. The well layer 25 having a larger lattice constant than the lattice constant of InP appears at a diffraction position smaller than the diffraction position of InP. The twelfth electron diffraction image is employed because it is possible to measure a lattice strain of the barrier layer 24 and the well layer 25 in high resolution. It is preferable to employ an electron diffraction image of higher order. However, it is not possible to obtain desired electron diffraction intensity from an electron diffraction image of higher order. Therefore, the twelfth electron diffraction image is employed as an electron diffraction image of an optimum order.

Thereafter, the reference profile calculating section 54 calculates a reference profile (step S203). This reference profile may be obtained in advance by calculation. The calculation of this reference profile is carried out as follows. First, when a scattering amplitude is expressed as F, electron diffraction intensity I shown in the diffraction intensity profile can be expressed by the square of an absolute value of the scattering amplitude F, as shown in the following equation (1).

$$I=|F|^2 \qquad (1)$$

Further, this scattering amplitude F can be expressed by the following equation (2).

$$F(K) = \sum_j f_j(K)\exp(2\pi i K \cdot R_j) \qquad (2)$$

For example, when (001) is a diffraction plane, this can be expressed by the following equation (3).

$$F(001) = \sum_{p=1}^{p} \exp\{2\pi i l(ma+nb)d_0 p\} \quad (3)$$

$$\left[\sum_{m=1}^{m} \exp\{2\pi i l(mad_0)\}\right.$$

$$f_{Aj}\sum_{j=1}^{4} \exp\left\{2\pi i lad_0(j-1)/2 + \sum_{j=1}^{n} \exp\{2\pi i l(mad_0+nbd_0)\}\right.$$

$$\left. f_{Bj}\sum_{j=1}^{4} \exp[2\pi i l\{mad_0+bd_0(j-1)/2\}]\right]$$

$$= \sum_{p=1}^{p} \exp\{2\pi i l(ma+nb)d_0 p\}$$

$$\left[F_A \sum_{m=1}^{m} \exp\{2\pi i l(mad_0)\} + \right.$$

$$\left. F_B \exp(2\pi i lmad_0) \sum_{n=1}^{n} \exp(2\pi i lnbd_0)\right]$$

$$= G_S\{G_A F_A + G_B F_B \exp(2\pi i lmad_0)\}$$

where, $$G_S = \frac{\sin\pi lp(ma+nb)d_0}{\sin\pi l(ma+nb)d_0}$$

$$G_A = \frac{\sin\pi lmad_0}{\sin\pi lad_0}$$

$$G_B = \frac{\sin\pi lnbd_0}{\sin\pi lbd_0}$$

$$F_A = f_{Aj}\sum_{j=1}^{4} \exp\{2\pi i lad_0(j-1)/2\}$$

$$F_B = f_{Bj}\sum_{j=1}^{4} \exp\{2\pi i lbd_0(j-1)/2\}$$

Figure 11:
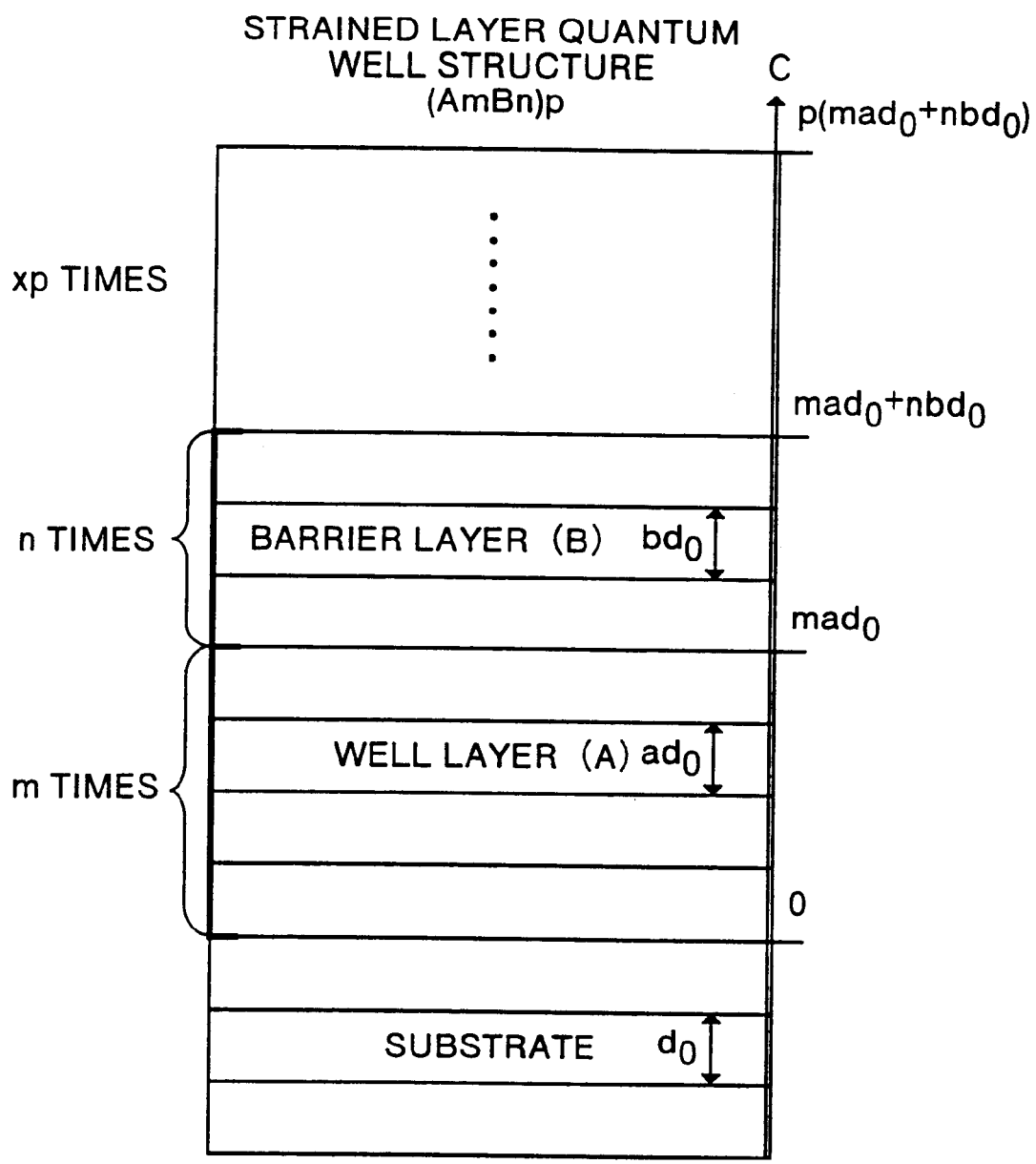
FIG. 11 is a schematic diagram of a strained layer quantum well structure used for calculating a reference profile.

The above equation (3) shows a scattering amplitude of the strained layer quantum well structure (AmBn) p that has a repetition by p times of the well layer 25 having a well layer "A" laminated by m using one molecular layer in the (001) direction as a unit, and the barrier layer 24 having a barrier layer "B" laminated by n using one molecular layer in the (001) direction as a unit, as shown in FIG. 11. In the above equation (3), $d_0$ denotes a period of a substrate (InP) using one molecular layer in the (001) direction as a unit, ado denotes a period of the well layer "A", and $bd_0$ denotes a period of the barrier layer "B". Further, "a" denotes the strain of the well layer, and "b" denotes the strain of the barrier layer. Further, in the above equation (3), $G_S$, $G_A$, and $G_B$ denote a super lattice, and Laue functions of the A layer and the B layer respectively. Based on the above, it is possible to calculate the detailed reference profile 57e.

Thereafter, the optimum profile preparing section 55 executes a peak fitting of the reference profile 57e to the diffraction intensity profile 57b, and prepares the optimum profile 57c (step S204). Further, the lattice-constant/strain calculating section 56 calculates the average lattice constant and the strain, based on this optimum profile (step S205), and outputs a result of this calculation from the output section 60 (step S206). Then, the process returns to step S105.

Figure 12:
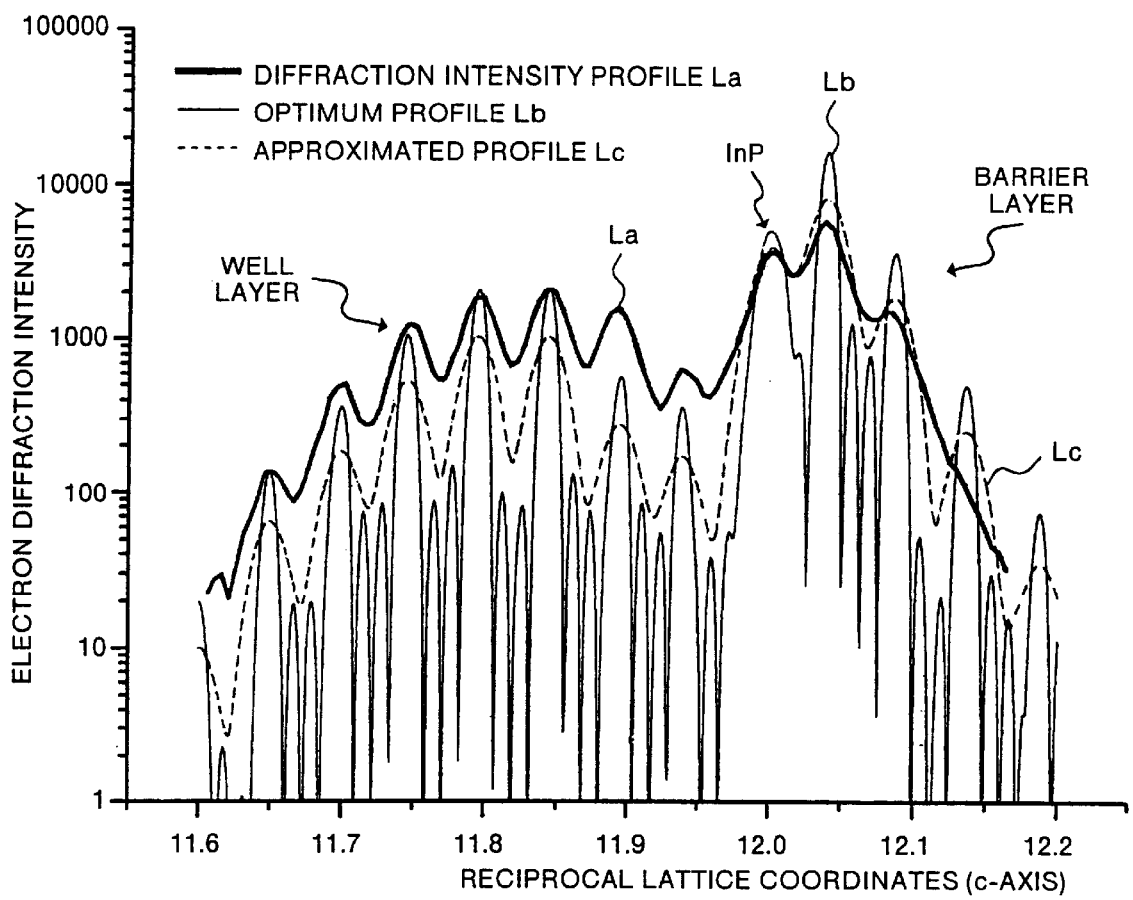
FIG. 12 is a diagram showing one example of a diffraction intensity profile and an optimum profile.

FIG. 12 is a diagram showing a detailed relationship between the diffraction intensity profile and the optimum profile in the twelfth electron diffraction image. In FIG. 12, a diffraction intensity profile La shown in a thick line is a profile prepared based on the raw data 57a of an electron diffraction image actually obtained. An optimum profile Lb shown in a thin line is a profile obtained as a result of peak-fitting the reference profile to the diffraction intensity profile La. As a result of this peak fitting, the average lattice constant of the well layer 25 is obtained as 0.5965 nm, the average lattice constant of the barrier layer 24 is obtained as 0.5816 nm, and the average lattice constant of InP (the p-InP blocking layer 7) is obtained as 0.5869 nm. Further, the average strain of the well layer 25 is obtained as +1.65 (%) based on InP, and the average strain of the barrier layer 24 is obtained as −0.90 (%) based on InP. The average lattice constants and the average strains can be obtained as described above because the value of the parameters "a" and "b" are determined by the peak fitting in the equation (3).

An approximated profile Lc shown in a broken line in FIG. 12 is a profile obtained by smoothing the optimum profile Lb by taking into account a spread of electron beams. It can be confirmed that this approximated profile comes nearer to the diffraction intensity profile La, and the determination of the optimum profile Lb is correct.

While the horizontal axis shown in FIG. 12 is expressed in the reciprocal lattice coordinates, the values on this axis are equivalent to the diffraction positions (pixel values) in the raw data. All crystals have two lattices, that is, a crystal lattice and a reciprocal lattice, respectively. This is because the diffraction pattern of a crystal is map of a reciprocal lattice of the crystal. Therefore, when the field-emission transmission electron microscope has sufficient resolution, it is possible to understand the reciprocal lattice as a map of a crystal structure in the actual space. A vector within an actual lattice has a dimension of length, and a vector within a reciprocal lattice has a dimension of 1/length. This is because the reciprocal lattice is a lattice of a Fourier space relating to this crystal.

According to the first embodiment, when a semiconductor laser element has a multi-layer film structure in a nano-meter order in a fine area like a strained layer quantum well structure, it is possible to irradiate a highly parallel flux of electron beams onto a specimen by using a field-emission transmission electron microscope of which condenser angle to the specimen has been adjusted to 0.5 mrad or below, and an electron-beam diameter has been adjusted to 20 to 100 nm to have a fine electron-beam flux. Therefore, it is possible to simultaneously measure lattice constants of layers that constitute a multi-layer film structure, and it is possible to obtain the lattice constant of the respective layers promptly and in high precision. Particularly, when a crystal structure of known InP exists that is disposed near a strained layer quantum well structure and the lattice constant of which is close to the lattice constant of the well layer and the barrier layer, it is possible to measure this InP together with the electron diffraction image of the strained layer quantum well structure. Based on this, it is possible to use the lattice constant of this InP as a scale of an absolute lattice constant, which makes it possible to measure lattice constants in higher precision.

Further, according to the first embodiment, the lattice constants of the well layers and the barrier layers that constitute the strained layer quantum well structure are measured at the same time. Therefore, as compared with the case of discretely and sequentially measuring the lattice constants of the well layers and barrier layers, it is possible to stabilize the measuring condition, and it is possible to measure lattice constants, particularly, average lattice constants and average strains, in higher precision.

As a second embodiment of the present invention, the field-emission transmission electron microscope in the first embodiment is further provided with an energy filter.

Figure 13:
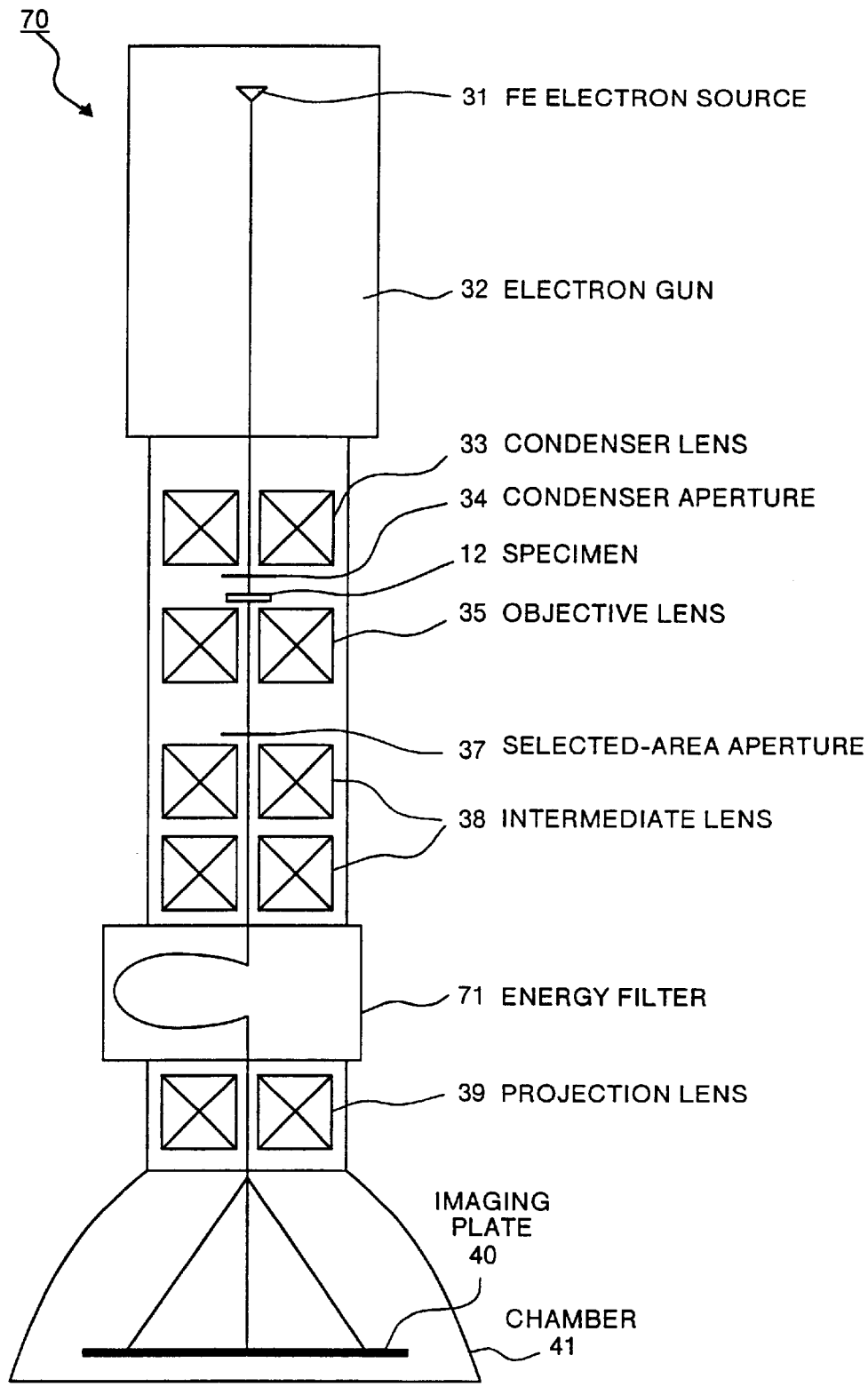
FIG. 13 is a cross-sectional view showing a structure of a field-emission transmission electron microscope according to a second embodiment of the invention.

FIG. 13 is a cross-sectional view showing an outline structure of a field-emission transmission electron microscope according to the second embodiment of the invention. The field-emission transmission electron microscope 70 has the in-column type energy filter 71 provided between the intermediate lens 38 and the projection lens 39 of the field-emission transmission electron microscope 30 explained in connection with the first embodiment. All other structures are identical with those of the first embodiment, and those identical portions are attached like reference numbers.

Since the energy filter 71 been provided, it is possible to remove in elastic scattering electron beams with lower energy than that of elastic scattering electron beams. With this arrangement, it is possible to reduce noise components of an electron diffraction image, and to obtain an electron diffraction image in higher precision. The energy filter 71 may be an in-column type energy filter. Based on this, it is possible to obtain an electron diffraction image having a larger diffraction angle, which makes it possible to utilize an electron diffraction image of higher order.

Further, based on the provision of this energy filter 71, it is possible to use a specimen 12 having a larger thickness. At present, it is necessary to reduce the thickness of the specimen to about 100 nm. When the specimen has a large thickness, strong background noise is formed on the electron diffraction image due to the in elastic scattering electron beams, and this deteriorates the precision of analysis.

On the other hand, when the specimen has a smaller thickness, a stress relaxation occurs in the multi-layer film structure portion, which relaxes the strain. As a result, there is risk that it is not possible to measure in high precision lattice constants of a multi-layer film disposed on the MQW active layer of an actual semiconductor laser element. However, based on the provision of the energy filter 71, and further based on a reduced thickness of the specimen, it is possible to reduce the occurrence of in elastic scattering electron beams, and it is possible to reduce the relaxation of the strain. As a result, it is possible to obtain electron diffraction images in high precision.

Figure 14:
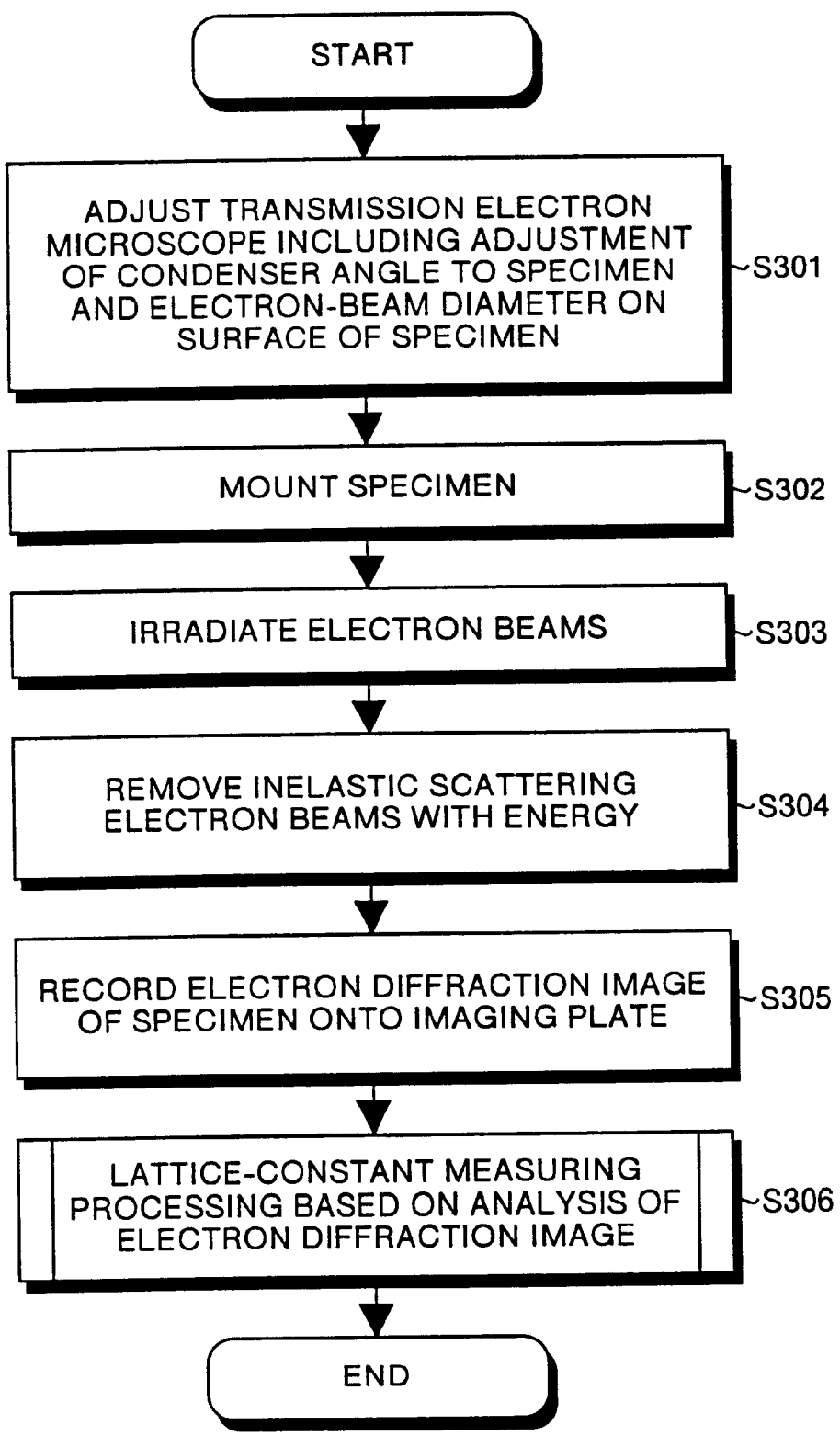
FIG. 14 is a flowchart showing a processing procedure of a method of measuring a lattice constant according to the second embodiment of the invention.

FIG. 14 is a flowchart showing a method of measuring a lattice constant according to the second embodiment of the invention. The procedure according to the second embodiment is the same as that of the first embodiment, except the removal processing of in elastic scattering electron beams by the energy filter 71 (step S304) that is inserted into between step S103 and step S104 shown in FIG. 5. Steps S301 to S303 in FIG. 14 correspond to steps S101 to S103 shown in FIG. 5 respectively, and steps S305 and S306 in FIG. 14 correspond to steps S104 and S105 shown in FIG. 5 respectively.

According to this second embodiment, as the energy filter is provided to remove in elastic scattering electron beams, it is possible to use a thick specimen. As the specimen can have little relaxation of strain, it is possible to obtain an electron diffraction image in higher precision.

Preparing a computer program for making a computer execute the above method of measuring a lattice constant also falls within a technical range of the present invention. The various processes involved in the method according to this invention may be realized on a computer by writing a computer program and executing this computer program on the computer. The computer program may be stored on a computer readable recording medium such as floppy disk, CD ROMs, or computer hard disks, and the computer is made to read the computer program from these recording medium. Alternately, the computer program may be made available over the Internet for download.

As explained above, according to one aspect of the present invention, a flux of highly parallel electron beams are irradiated onto a specimen having a multi-layer film structure in a nano-meter order. An electron diffraction image diffracted from the specimen is recorded onto a photosensitive member. The recorded electron diffraction image is analyzed, and a lattice constant of a multi-layer film structure of the specimen is measured based on a result of this analysis. Therefore, it is possible to measure lattice constants of a multi-layer film structure in a nano-meter order simultaneously and under the same condition. As a result, there is an effect that, as compared with the case of separately measuring each lattice constant of each film that constitutes a multi-layer film structure, it is possible to measure the lattice constants more quickly and in higher precision.

Furthermore, as the multi-layer film structure in the nano-meter order is in a strained layer quantum well structure, it is possible to measure lattice constants and strains of the strained layer quantum well structure simultaneously and under the same condition. Therefore, there is an effect that it is possible to measure lattice constants promptly and in high precision, and it is also possible to measure an average strain of the strained layer quantum well structure in high precision.

Moreover, as the period of the strained layer quantum well structure is set to 5 to 50 nm, and average lattice constants and average strains of barrier layers and well layers of the strained layer quantum well structure are measured respectively, there is an effect that it is possible to measure the average lattice constants and the average strains promptly and in high precision even when the strained layer quantum well structure is a multi-layer film structure having a fine repetitive period.

Furthermore, there is provided a condenser aperture at an electron beam source side of the specimen, thereby to irradiate a fine flux of electron beams having a condenser angle of 0.5 mrad or below and having an electron-beam diameter of 20 nm to 100 nm, onto the specimen. Specifically, a flux of parallel electron beams are irradiated onto the specimen, thereby to make it possible to simultaneously measure the layers of the strained layer quantum well structure. Therefore, it is possible to measure a multi-layer film structure like the strained layer quantum well structure simultaneously and under the same condition, and it is possible to obtain electron diffraction images in high resolution. As a result, there is an effect that it is possible to achieve measurement promptly and in high precision.

Moreover, the flux of electron beams are irradiated simultaneously onto a multi-layer film in a nano-meter order and a single material adjacent to this multi-layer film and having a known lattice constant. Therefore, there is an effect that it is possible to measure lattice constants and strains in high precision based on the known reference lattice constant shown by this single material.

Furthermore, after the above irradiation process, in elastic scattering electron beams are deleted by using an energy filter from among diffraction electron beams that have passed through the specimen. Therefore, it is possible to reduce the in elastic scattering electron beams that become noise components of the electron diffraction image. At the same time, it is possible to use a thick specimen. As a result, there is an effect that there is no relaxation in the strain of the specimen, and it is possible to measure lattice constants and strains in higher precision.

Moreover, an electron diffraction image is recorded by using an imaging plate having a dynamic range of 100 thousand times or above. Therefore, there is an effect that it is possible to read securely the electron diffraction images of the layers of the multi-layer film structure.

Furthermore, diffracted waves of a substrate orientation that is the same as the growth direction of each layer of the multi-layer film are recorded. Therefore, there is an effect that it is possible to obtain an electron diffraction image of each layer of the repeated multi-layer film structure.

Moreover, at the lattice-constant measuring process, at the reading process, an electron diffraction image recorded on the photosensitive member is read as digital data. At a profile obtaining process, a diffraction intensity profile of the diffracted wave is obtained based on the digital data read at the reading process. At the profile calculating process, a calculated diffraction intensity profile corresponding to the diffraction intensity profile is obtained, based on a predetermined arithmetic expression that includes known data of the multi-layer film structure in a nano-meter order. At the lattice-constant determining process, the calculated diffraction intensity profile that most matches the diffraction intensity profile is obtained, and a plurality of lattice constants that constitute each multi-layer film are determined from parameters of the arithmetic expression of the calculated diffraction intensity profile. Therefore, there is an effect that it is possible to obtain in high precision lattice constants of layers that constitute each multi-layer film, based on the profile obtained from the electron diffraction image.

According to another aspect of the present invention, the apparatus for measuring a lattice constant that irradiates a flux of electron beams onto a specimen, records an electron diffraction image based on diffraction electron beams that have passed through the specimen, analyses this electron diffraction image and measures a lattice constant of the specimen. Moreover, there is provided the condenser aperture at an electron beam source side of the specimen having a strained layer quantum well structure, thereby to irradiate a fine flux of electron beams having a condenser angle of 0.5 mrad or below and having an electron-beam diameter of 20 nm to 100 nm, onto the specimen. Therefore, it is possible to measure lattice constants of a multi-layer film structure in a nano-meter order simultaneously and under the same condition. As a result, there is an effect that, as compared with the case of separately measuring each lattice constant of each film that constitutes a multi-layer film structure, it is possible to measure the lattice constants more quickly and in higher precision.

Furthermore, there is provided an energy filter. With this energy filter, in elastic scattering electron beams are deleted from among diffraction electron beams that have passed through the specimen, and noise components due to the in elastic scattering electron beams are removed. Therefore, it is possible to obtain electron diffraction images in high precision, and it is also possible to have a thick specimen. As a result, there is an effect that it is possible to avoid relaxation in the strain of the multi-layer film structure, and it is possible to obtain electron diffraction images in higher precision.

Moreover, the electron diffraction images are recorded by using an imaging plate having a dynamic range of 100 times or above. Therefore, it is possible to use high-order electron diffraction images in high resolution. As a result, there is an effect that it is possible to measure lattice constants in higher precision.

Furthermore, the reading unit reads an electron diffraction image recorded on the imaging plate, as digital data. A profile obtaining unit obtains a diffraction intensity profile of the diffracted waves of a substrate orientation that is the same as the film growth direction of a strained layer quantum well structure, based on the digital data read by the reading unit. The profile calculating unit obtains a calculated diffraction intensity profile corresponding to the diffraction intensity profile, based on a predetermined arithmetic expression that includes known data of the strained layer quantum well structure. The strain calculating unit obtains the calculated diffraction intensity profile that most matches the diffraction intensity profile, and calculates strain values of well layers and barrier layers of the strained layer quantum well structure from parameters of the arithmetic expression of the calculated diffraction intensity profile. Therefore, it is possible to calculate average strains of the well layers and the barrier layers in high precision. As a result, there is an effect that it is possible to specify laser characteristics of a semiconductor laser element that has a strained layer quantum well structure.

Although the invention has been described with respect to a specific embodiment for a complete and clear disclosure, the appended claims are not to be thus limited but are to be construed as embodying all modifications and alternative constructions that may occur to one skilled in the art which fairly fall within the basic teaching herein set forth.

What is claimed is:

1. A method of measuring a lattice constant, the method comprising the processes of:

irradiating a flux of highly parallel electron beams onto a specimen having a multi-layer film structure in a nano-meter order;

recording a transmission electron diffraction image diffracted from the specimen onto a photosensitive member, the image showing a spatial variation of the intensity of the electron diffraction pattern; and analyzing the recorded transmission electron diffraction image, and measuring the value of a lattice constant of a multi-layer film structure of the specimen based on a result of the analysis.

2. The method according to claim 1, wherein the multi-layer film structure in a nano-meter order is a strained layer quantum well structure.

3. The method according to claim 2, wherein a period of the strained layer quantum well structure is 5 to 50 nm.

4. The method according to claim 1, wherein at the irradiation process, there is provided a condenser aperture at an electron beam source side of the specimen, thereby to irradiate onto the specimen a fine flux of electron beams having a condenser angle of 0.5 mrad or below and having an electron-beam diameter of 20 nm to 100 nm.

5. The method according to claim 1, wherein at the irradiation process, the flux of electron beams are irradiated simultaneously onto the multi-layer film in a nano-meter order and a single material adjacent to this multi-layer film and having a known lattice constant, the single material having a boundary with at least two layers of the multi-layer film and having a composition which is different from at least one of the layers of the multi-layer film.

6. The method according to claim 1, further comprising the process, during the irradiation process, of deleting inelastic scattering electron beams by using an energy filter from among diffraction electron beams that have passed through the specimen.

7. The method according to claim 1, wherein at the recording process, a transmission electron diffraction image is recorded by using an imaging plate having a dynamic range of 100 thousand times or above.

8. The method according to claim 1, wherein at the recording process, diffracted waves of a substrate orientation that is the same as the growth direction of each layer of the multi-layer film are recorded.

9. The method according to claim 1, wherein the lattice-constant analyzing/measuring process comprises the processes of:
   reading a transmission electron diffraction image recorded on the photosensitive member as digital data;
   obtaining an empirical diffraction intensity profile of the diffracted wave based on the read digital data;
   calculating a diffraction intensity profile corresponding to the empirical diffraction intensity profile, based on a predetermined arithmetic expression that includes known data of the multi-layer film structure in a nano-meter order; and
   obtaining a calculated diffraction intensity profile that most matches with the empirical diffraction intensity profile, and determining a plurality of lattice constants that constitute each multi-layer film from parameters of the arithmetic expression of the calculated diffraction intensity profile.

10. The method according to claim 1 wherein the transmission electron diffraction image comprises an order which is higher than the zero-order diffraction image.

11. A method of measuring a lattice constant, the method comprising the steps of:
   irradiating a portion of a multi-layer film structure with a flux of parallel electron beams to generate an electron diffraction pattern;
   recording an image of the transmission electron diffraction pattern, the recorded image showing a spatial variation of the intensity of the electron diffraction pattern;
   generating an intensity profile of at least a portion of the recorded image, the intensity profile showing a spatial variation of the intensity of the electron diffraction pattern;
   generating a reference profile for said portion of the recorded image, the reference profile being based on an arithmetic expression that includes known data for the irradiated portion of the multi-layer film and at least one parameter related to at least one lattice constant of the multi-layer film, said reference profile showing a spatial variation of the intensity of the electron diffraction pattern; and
   generating a measured value of the at least one lattice constant of the multi-layer film from the intensity profile and the reference profile.

12. The method of claim 11 wherein the step of generating the measured value of the at least one lattice constant comprises the step of comparing the spatial variations of the intensity profile and the reference profile.

13. The method of claim 12 wherein the step of generating the measured value of the at least one lattice constant comprising the steps of:
   adjusting the value of the at least one parameter to increase the matching of the spatial variations of the reference profile to the spatial intensity variations of the intensity profile; and
   generating the measured value of the at least one lattice constant from the adjusted value of the at least one parameter.

14. The method according to claim 11, wherein the multi-layer film structure comprises a strained layer quantum well structure.

15. The method according to claim 14, wherein a period of the strained layer quantum well structure is 5 to 50 nm.

16. The method according to claim 11, wherein at the irradiation step, there is provided a condenser aperture at an electron beam source side of the specimen, thereby to irradiate onto the specimen a fine flux of electron beams having a condenser angle of 0.5 mrad or below and having an electron-beam diameter of 20 nm to 100 nm.

17. The method according to claim 11, wherein at the irradiation step, the flux of electron beams are irradiated simultaneously onto the multi-layer film and a single material adjacent to this multi-layer film and having a known lattice constant.

18. The method according to claim 11, wherein the irradiation step further comprises the step of deleting inelastic scattering electron beams by using an energy filter from among diffraction electron beams that have passed through the specimen.

19. The method according to claim 11, wherein at the recording step, a transmission electron diffraction image is recorded by using an imaging plate having a dynamic range of 100 thousand times or above.

20. The method according to claim 11, wherein at the recording steps, diffracted waves of a substrate orientation that is the same as the growth direction of each layer of the multi-layer film are recorded.

* * * * *